United States Patent
Viswanadham et al.

(10) Patent No.: US 8,722,573 B2
(45) Date of Patent: May 13, 2014

(54) SULFONATED CARBON SILICA COMPOSITE MATERIAL AND A PROCESS FOR THE PREPARATION THEREOF

(71) Applicant: Council of Scientific & Industrial Research, New Delhi (IN)

(72) Inventors: Nagabhatla Viswanadham, Uttrakhand (IN); Devaki Nandan, Uttrakhand (IN)

(73) Assignee: Council of Scientific & Industrial Research, New Delhi (IN)

( * ) Notice: Subject to any disclaimer, the term of this patent is extended or adjusted under 35 U.S.C. 154(b) by 41 days.

(21) Appl. No.: 13/623,775

(22) Filed: Sep. 20, 2012

(65) Prior Publication Data

US 2014/0057778 A1    Feb. 27, 2014

(30) Foreign Application Priority Data

Aug. 22, 2012   (IN) .............. 2597/DEL/2012

(51) Int. Cl.
*B01J 21/04*    (2006.01)
*B01J 23/02*    (2006.01)

(52) U.S. Cl.
USPC ........ 502/439; 502/168; 502/233; 423/445 R; 423/353

(58) Field of Classification Search
USPC ............................................... 423/445 R, 338
See application file for complete search history.

(56) References Cited

U.S. PATENT DOCUMENTS

| | | | | |
|---|---|---|---|---|
| 5,827,903 | A   * | 10/1998 | White et al. ................. | 518/710 |
| 6,822,005 | B2 * | 11/2004 | Font Freide et al. .......... | 518/712 |
| 7,678,732 | B2 * | 3/2010  | Chen et al. ................... | 502/220 |
| 8,114,915 | B2 * | 2/2012  | Hammond et al. ........... | 518/700 |
| 2004/0180976 | A1 * | 9/2004 | Hensman et al. ............. | 518/726 |
| 2005/0182145 | A1 * | 8/2005 | Mohedas et al. ............. | 518/716 |

* cited by examiner

*Primary Examiner* — Melvin Curtis Mayes
*Assistant Examiner* — Melissa Stalder
(74) *Attorney, Agent, or Firm* — Knobbe, Martens, Olson & Bear, LLP

(57) ABSTRACT

The present invention relates to a novel sulfonated carbon silica (SCS) composite material and a process for the preparation thereof. The synthesized SCS composite material on calcination yields the hierarchical mesoporous silica (MS) and further finds application as catalyst in two industrially important reactions namely phenol butylation and glycerol acetalization.

17 Claims, 7 Drawing Sheets

SULFONATED CARBON SILICA COMPOSITE MATERIAL AND A PROCESS FOR THE PREPARATION THEREOF

FIELD OF THE INVENTION

The present invention relates to a novel sulfonated carbon silica (SCS) composite material and a process for the preparation thereof. The synthesized SCS composite material on calcination yields the hierarchical mesoporous silica (MS) and further finds application as catalyst in two industrially important reactions namely phenol butylation and glycerol acetalization.

BACKGROUND OF THE INVENTION

Currently, mesoporous materials are gaining importance for catalytic applications due to facile diffusion of molecules in their pores and for transformation of large, bulky molecules through catalysis. The immobilization of homogeneous catalyst on to the mesoporous solid surface is one of the vital applications of the mesoporous materials as the composite catalyst can give higher acidity while eliminating the complications involved in handling and separation of liquid acids that generally occur in multiple steps and which are time consuming. Particularly, the mesoporous silica obtained is finding variety of applications such as gas adsorption and for incorporation of metal to prepare bi-functional catalysts for various catalytic applications.

However, the art of synthesis requires specific preparation procedures that necessarily involve use of high cost ionic surfactants and block co-polymers as templating agents to drive the reactants towards the structure specific mesopores. Moreover, such template materials are also harmful and needs additional synthesis steps performed at high temperatures for template removal before using them for catalytic applications. The art of catalyst design lies in obtaining the well dispersed active sites in a high surface area porous material. Further, art of synthesis requires multiple step procedure following carbonization followed by sulfonation steps that limits the amount of acid bearing carbon sites (sulfonyl groups) which are required for the catalytic activity.

References may be made to U.S. Pat. No. 7,014,799 and U.S. Pat. No. 7,763,665 that describe the synthesis of mesoporous oxides where amphiphilic block copolymer is used as templating agent. However, the said process uses costly amphiphilic block copolymer and also involves lengthy procedure.

Reference may be made to US patent publication number 20050063890 that describes formation of mesoporous mixed oxide such as porous silica using amphiphilic surfactant as template. However, the drawback of this process lies in obtaining good connectivity between the macro pores and mesopores and exhibits broad distribution of pores.

References may be made to U.S. Pat. No. 6,696,258 that describes synthesis of various mesoporous oxides such as silica, alumina using glucose and other monosaccharides. But the process involves lengthy reaction time and procedures with steps such as pH adjustment with base and solvent extraction of the inner material to obtain the porous solids.

Reference may be made to S. Van de Vyver, L. Peng, J. Geboers, H. Schepers, F. de clippel, C. J. Gommes, B. Goderis, P. A. Jacobs and B. F. Sels, *Green Chem.*, 2010, 12, 1560, where expensive block copolymer is used as a carbon source with two separated multiple steps procedure involving carbonization followed by sulfonation to obtain the acid functionality in the catalyst. The limitation of this process involves the use of expensive material and the two separated step procedure, one involving carbonization and the other involving sulfonation, limits the amount of acid sites that are required for the catalytic applications.

Reference may be made to P. Gupta and S. Paul, *Green Chem.*, 2011, 13, 2365 where variety of mono and disaccharides are used as carbon source. But the method follows two separated step procedure, one involving carbonization and the other involving sulfonation that limits the formation high number of acid sties on the already carbonized material.

Further, the alkylation of phenol and the conversion of Glycerol into solketal (ketal of glycerol) are of great industrial importance. Some 450,000 tonnes of alkylated products like tertiary butyl phenols are used in the industry per year. Mono-alkyl phenols and di-alkylphenols are used in the manufacture of antioxidants, UV absorbers and for the production of phenolic resins. Literature review reveals that these alkylation reactions are mostly carried out in the gas phase with high conversion of phenol. However, gas phase reactions usually involve high temperature and pressure leading to high cost. Very few studies on the solvent state alkylation of phenol with tertiary butyl alcohol (TBA) have been published. These solvent state reactions however, usually show very low conversions, i.e., less than 50%. It will therefore be advantageous to find new environmental friendly catalysts and milder experimental conditions to increase output or to reduce cost or to satisfy the environmental needs.

Reference may be made to K. R. Sunajadevi and S. Sugunan, *Catalysis Letters*, 2005, 99, 3 where sulfated titania is used as catalyst for the tertiary butylation of phenol in vapour phase from temperature 453 K. However, the catalyst is not effective as it gives limited phenol conversion only up to 36% (wt. %).

Reference may be made to L. Li, T. I. Korányi, B. F. Sels and P. P. Pescarmona, *Green Chem.*, 2012, 10.1039/c2gc16619d where heterogeneous Lewis acid catalysts such as Zr-TUD-1, Hf-TUD-1, Al-TUD-1,Sn-MCM-41 and USY were used for the production of solketal by facilitating reaction between glycerol and acetone at 353 K. However, these catalysts are not very effective due to limited glycerol conversions and time taken for this reaction is very high (6 h).

Reference may be made to G. Vicente, J. A. Melero, G. Morales, M. Paniagua and E. Martin, *Green Chem.*, 2010, 12, 899 where sulfonic acid modified silca samples were used for the production of solketal from glycerol at 343 K. Though the catalysts exhibited higher glycerol conversions 85% (mol %), the cost involved in the synthesis of catalyst is high with lengthy synthesis procedures.

Based on the prior art details and drawback mentioned above, the object of the present invention is to provide a novel sulfonated carbon silica (SCS) composite material and a process for the preparation of such SCS composite material. Another object of the present invention is to provide at least one industrial application of the novel SCS composite material thus developed.

SUMMARY OF THE INVENTION

Accordingly, the present invention provides a novel sulfonated carbon silica (SCS) composite material comprising a hydrophobic inner core formed of carbons and a hydrophilic shell formed of silica matrix, said carbon being present in the range of 18% to 54% and silica in the range of 46 to 82%; said hydrophobic inner core formed of carbon atoms bearing thereupon hydrophilic sulfonyl groups, wherein amount of sulfonyl groups present is such that it imparts an overall acidity at least about 0.6 m, mol $NH_3$/g catal to the Sulfonated carbon silica (SCS) composite material, and wherein the ratio between the total BET surface area to the mesopore surface area is in the range of 1.09 to 2.8; and the micropore surface area to the mesopore surface area is in the range of 0.09 to 1.82.

In an embodiment of the present invention, the SCS composite material exhibits surface area in the range of 150-800 m²/g.

In another embodiment of the present invention, the SCS composite material exhibit mesopore diameter in the range of 2.6 to 15 nm.

In yet another embodiment of the present invention, the SCS composite material exhibits surface area of about 650 m²/g.

In still another embodiment of the present invention, the SCS composite material exhibits and mesopore diameter of about 5.6 nm.

In a further embodiment of the present invention, the SCS composite material exhibits structural stability up to about 573 K as determined by Thermo Gravimetric Analysis.

In a furthermore embodiment of the present invention the SCS composite material finds application as a starting material for preparation of mesoporous silica material and application as catalyst in phenyl butylation reaction and glycerol acetylation reaction.

The present invention also provides a process (100) of preparing the sulfonated carbon silica (SCS) composite material, said process comprising the steps of:
(a) gradually mixing a saccharide with a silica source and sulfuric acid to form a mixture (step 101, refer to FIG. 1);
(b) allowing a hydrolyzing reaction to progress in the mixture to obtain a gel (step 102, refer to FIG. 1); and
(c) simultaneously performing carbonization and sulfonation reactions on the gel to obtain the sulfonated carbon silica composite (step 103, refer to FIG. 1).

In an embodiment, the process of the present invention further comprises a step of drying the gel thus obtained in step (b).

In another embodiment of the present invention, a ratio between saccharide and the silica source is in the range of about 0.385 to about 4.25.

In yet another embodiment of the present invention, a quantity of sulphuric acid is in the range of 0.234 to 1.020 M.

In still another embodiment of the present invention, the reaction mixture in step (b) is maintained at a temperature in the range of about 298 K to 320 K for a period in the range of about 2 to about 5 hours to effect hydrolyzation (step 104, refer to FIG. 2).

In a further embodiment of the present invention, step (c) comprises:
c1. treating the gel as obtained in step (b) at a temperature in the range of about 350 K to about 423 K for a period in the range of about 12 hours to about 18 hours to obtain a bulk solid mass (step 105, refer to FIG. 3); and
c2. heating the bulk solid mass as obtained in (i) at a temperature in range of about 473 K to about 573 K for a period in the range of about 4 hours to about 8 hours under nitrogen gas to obtain the sulfonated carbon silica (SCS) composite (step 106, refer to FIG. 3).

In a furthermore embodiment of the present invention, step (c) comprises:
c3. treating the gel as obtained in step (b) inside a Teflon-lined autoclave at a temperature in the range of about 350 K to about 423 K for a period in the range of about 12 hours to about 18 hours to obtain bulk solid mass (step 107, refer to FIG. 4); and
c4. heating the bulk solid mass as obtained in (i) at a temperature in range of about 473 K to about 573 K for a period in the range of about 4 hours to about 8 hours under nitrogen gas to obtain the sulfonated carbon silica (SCS) composite (step 108, refer to FIG. 4).

In another embodiment, the process of the present invention further comprises washing the sulfonated carbon silica composite at least once.

In yet another embodiment, the process of the present invention further comprises drying the sulfonated carbon silica composite.

In still another embodiment of the present invention, the washing is carried out for a period in the range of about 2 hours to about 3 hours.

In a further embodiment of the present invention, the sulfonated carbon silica composite is initially dried at a temperature in the range of about 293 K to about 423 K for a period in the range of about 2 hours to about 6 hours and further dried at a temperature in the range of about 373 K to 403 about K for a period in the range of about 2 hours to about 6 hours.

In another embodiment of the present invention, the saccharide is selected from the group comprising of glucose, fructose and maltose.

In yet another embodiment of the present invention, the saccharide is glucose.

In still another embodiment of the present invention, the silica source is selected from the group comprising of fumed silica, tetra-methyl ortho-silicate and tetra-propyl ortho silicate.

In a further embodiment of the present invention, the silica source is tetra-ethyl ortho-silicate.

The present invention further provides a process of preparing a mesoporous silica material, said process comprising the steps of:
(a) gradually mixing a saccharide with a silica source and a sulphonizing agent to form a mixture;
(b) allowing a hydrolyzing reaction to progress in the mixture to obtain a gel;
(c) simultaneously performing carbonization and sulfonation reactions on the gel to obtain a sulfonated carbon silica composite; and
(d) calcining the sulfonated carbon silica composite to obtain mesoporous silica material.

The present invention furthermore provides a method for controlling one or more properties of a mesoporous silica material selected from the group comprising of micropore surface area, mesopore surface area, total surface area, micropore volume, mesopore volume and total pore volume average pore diameter, said method comprising the steps of:
(a) gradually mixing a saccharide with a silica source and a sulphonizing agent to form a mixture;
(b) allowing a hydrolyzing reaction to progress in the mixture to obtain a gel;
(c) simultaneously performing carbonization and sulfonation reactions on the gel to obtain a sulfonated carbon silica composite; and
(d) calcining the sulfonated carbon silica composite to obtain mesoporous silica material;
wherein:
(i) in step (a), a ratio between saccharide and the silica source is varied in the range of about 0.385 to about 4.25; OR (ii) in step (a), a quantity of the sulphonizing agent is varied in the range of 0.234 to 1.020 M; OR
(iii) a reaction condition under which the carbonization and sulfonation reactions is performed in step (c), is varied.

The present invention also provides a process for butylation of phenol, said process comprising contacting phenol, tertiary butyl alcohol and sulfonated carbon silica (SCS) composite material under reaction conditions to obtain tertiary butyl phenol; wherein the sulfonated carbon silica composite material acts as a catalyst and comprises a hydrophobic inner core formed of carbons and a hydrophilic shell formed of silica matrix, said carbon being present in the range of 18% to 54% and silica in the range of 46 to 82%; said hydrophobic inner core formed of carbon atoms bearing thereupon hydrophilic sulfonyl groups, wherein amount of sulfonyl groups present is such that it imparts an overall acidity at least about 0.6 m, mol $NH_3$/g catal to the Sulfonated carbon silica (SCS) composite material, and wherein the ratio between the total BET surface area to the mesopore surface area is in the range of 1.09 to 2.8; and the micropore surface area to the mesopore surface area is in the range of 0.09 to 1.82.

The present invention further provides a process for acetalization of glycerol, said process comprising contacting glycerol, acetone and sulfonated carbon silica (SCS) composite material under reaction conditions to obtain solketal; wherein the sulfonated carbon silica composite material acts as a catalyst and comprises a hydrophobic inner core formed of carbons and a hydrophilic shell formed of silica matrix, said carbon being present in the range of 18% to 54% and silica in the range of 46 to 82%; said hydrophobic inner core formed of carbon atoms bearing thereupon hydrophilic sulfonyl groups, wherein amount of sulfonyl groups present is such that it imparts an overall acidity at least about 0.6 m, mol $NH_3$/g catal to the Sulfonated carbon silica (SCS) composite material, and wherein the ratio between the total BET surface area to the mesopore surface area is in the range of 1.09 to 2.8; and the micropore surface area to the mesopore surface area is in the range of 0.09 to 1.82.

BRIEF DESCRIPTION OF THE DRAWINGS

A more complete appreciation of this invention will be understood by reference to the following detailed description when considered in conjunction with the accompanying drawings in which.

Figure 1:
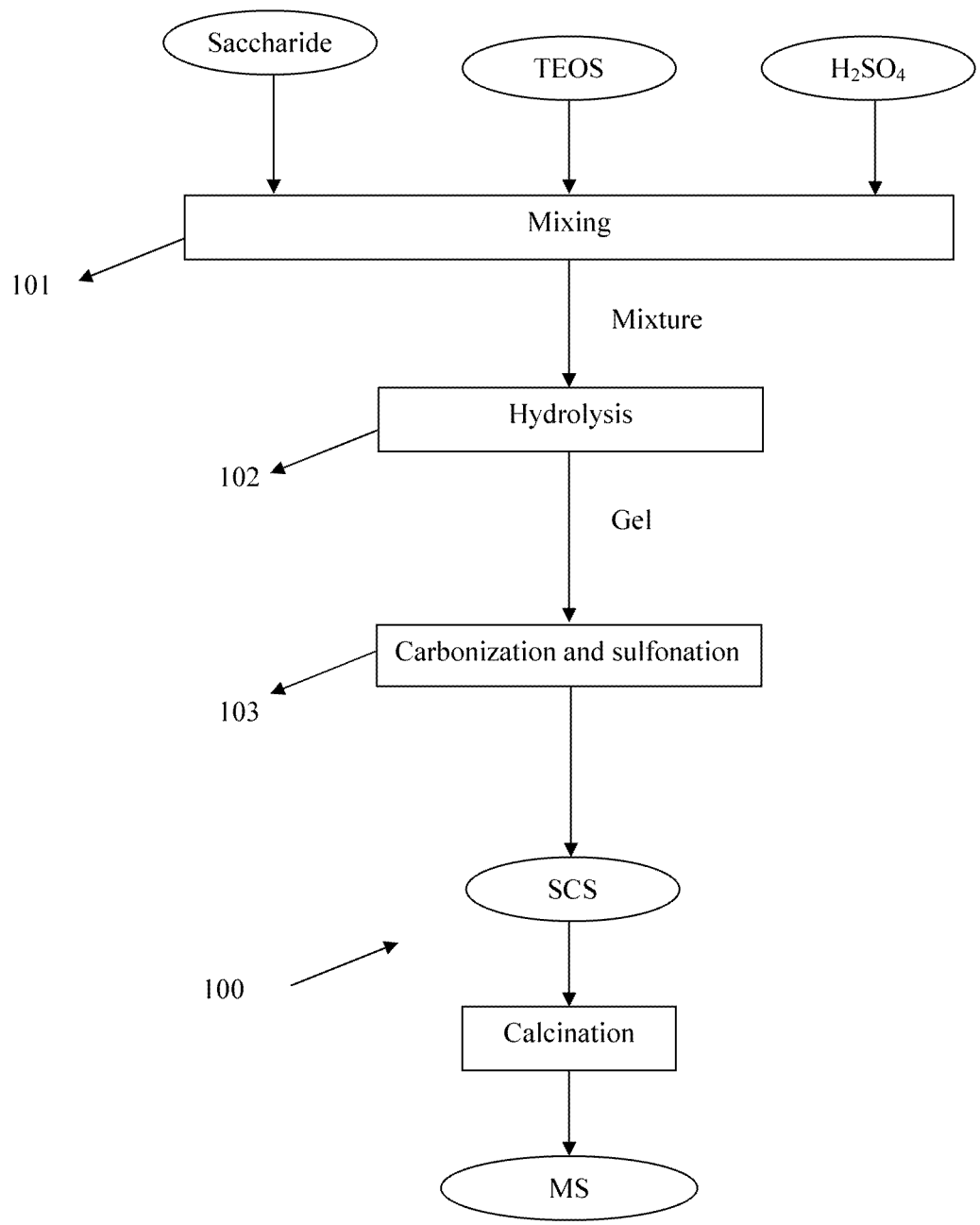
FIG. 1 represents is overall the flow chart of process for preparing the SCS composite material in accordance with the teachings of the present invention.

It may be noted that to the extent possible, like reference numerals have been used to represent like elements in the drawings. Further, skilled artisans will appreciate that elements in the drawings are illustrated for simplicity and may not have been necessarily been drawn to scale. For example, the dimensions of some of the elements in the drawings may be exaggerated relative to other elements to help to improve understanding of aspects of the present invention. Furthermore, the one or more steps may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION OF THE INVENTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternative falling within the spirit and the scope of the invention as defined by the appended claims.

The steps of the process have been represented where appropriate by conventional symbols in the drawings, showing only those specific details that are pertinent to understanding the embodiments of the present invention so as not to obscure the disclosure with details that will be readily apparent to those of ordinary skill in the art having benefit of the description herein.

The terms "comprises", "comprising", or any other variations thereof, are intended to cover a non-exclusive inclusion, such that a process, method that comprises a list of steps does not include only those steps but may include other steps not expressly listed or inherent to such process, method. Similarly, one or more elements proceeded by "comprises . . . a" does not, without more constraints, preclude the existence of other elements or additional elements in the composite material.

As described above, the present invention provides a sulfonated carbon silica (SCS) composite material comprising a hydrophobic inner core formed of carbons and a hydrophilic shell formed of silica matrix, said carbon being present in the range of 18% to 54% and silica in the range of 46 to 82%; said hydrophobic inner core formed of carbon atoms bearing thereupon hydrophilic sulfonyl groups, wherein amount of sulfonyl groups present is such that it imparts an overall acidity at least about 0.6 m, mol $NH_3$/g catal to the Sulfonated carbon silica (SCS) composite material, and wherein the ratio between the total BET surface area to the mesopore surface area is in the range of 1.09 to 2.8; and the micropore surface area to the mesopore surface area is in the range of 0.09 to 1.82.

The SCS composite material exhibits surface area in the range of 150-800 m$^2$/g and preferably of about 650 m$^2$/g and mesopore diameter in the range of 2.6 to 15 nm and preferably of about 5.6 nm. It has been confirmed by thermo gravimetric analysis (TGA) that the SCS composite material exhibit structural stability up to 573K. The SCS composite material finds multiple application some of which include (without restriction) use of the SCS composite material as a starting material for preparation of mesoporous silica material and use of the SCS composite material as catalyst in phenyl butylation reaction and in glycerol acetylation reaction.

As described above, the present invention also provides a process for preparing said sulfonated carbon silica (SCS) composite material, said process comprising the steps of:
(a) gradually mixing a saccharide with a silica source and a sulfuric acid to form a reaction mixture, wherein a ratio between saccharide and the silica source is in the range of about 0.385 to about 4.25 and a quantity of the sulphuric acid is in the range of 0.234 to 1.020 M;
(b) allowing a hydrolyzing reaction to progress in the mixture reaction by maintaining the reaction mixture at a temperature in the range of about 298 K to 320 K for a period in the range of about 2 to about 5 hours to effect hydrolyzation thereby to obtain a gel;
(c) treating the gel thus obtained in step (b) at a temperature in the range of about 350 K to about 423 K for a period in the range of about 12 hours to about 18 hours to obtain a bulk solid mass; and
(d) heating the bulk solid mass as obtained in (c) at a temperature in range of about 473 K to about 573 K for a period in the range of about 4 hours to about 8 hours under nitrogen gas to obtain the sulfonated carbon silica (SCS) composite.

Further, the process of step (c) optionally, comprises treating the gel as obtained in step (b) inside a Teflon-lined autoclave at a temperature in the range of about 350 K to about 423 K for a period in the range of about 12 hours to about 18 hours to obtain bulk solid mass;

In accordance with one preferred embodiment of the present invention, the process further comprises washing the sulfonated carbon silica composite with 2 to 8 liter of water for 2 to 3 hours to remove physically adsorbed sulfate ions, followed by its drying at 293 K to 423 K temperature for 2 to 6 hours and drying at 373 to 403 K for 2 to 6 hours to obtain dry SCS composite. In yet another embodiment of the present invention, said carbon source is selected from the group comprising of glucose, fructose, maltose and is preferably glucose. It has been observed that the use of glucose as a preferred carbon source facilitates the formation of sulfonated carbon silica composite (SCS) intermediate which upon calcinations gives the high surface area hierarchical mesoporous silica (MS).

In yet another embodiment of the present invention, the silica source is selected from the group comprising of fumed silica, tetra-methyl ortho-silicate, tetra-ethyl ortho-silicate, tetra-propyl ortho-silicate and is preferably tetra-ethyl ortho-silicate (TEOS).

In yet another embodiment of the present invention, sulfuric acid is used as source for sulfonyl groups. The SCS material is highly acidic and acidity can be varied by varying concentration of glucose and sulphuric acid.

In yet another embodiment of the present invention, said SCS composite material produces high surface area hierarchical mesoporous silica (MS) material on simple calcinations at a temperature in the range of 773 K to 873 K for a period in the range of 6 to 10 hours.

In yet another embodiment of the present invention, said MS material exhibits high surface area ranging from 300-800 m$^2$/g, preferably 550 m$^2$/g and flexibility in mesopore diameter range from 5 to 20 nm, preferably 5.6 nm.

In still another embodiment, in the above process described involves simultaneous carbonization and sulfonation of glucose in presence of organic silica moiety to give high surface area, highly acidic sulfonated carbon-silica-composite (SCS) that up on simple calcination yields MS. Such a process for simultaneous simultaneous carbonization and sulfonation has not been envisaged by any prior art document. Particularly, the process described in the present invention is an efficient method through the generation of active sulfonyl groups to facilitate the effective interaction between the hydrophobic carbon and the hydrophilic silica so as to yield the hierarchical mesoporous silica. Thus, it can be said that the process described in the present application is simpler and cheaper method for making the CSC composite material and mesoporous silica material both of which can have desired pore diameter. Controlling the porosity in the SCS composite material and the MS material is attained by controlling composition of a gel (which is formed in the initial steps described in the process and more particularly by controlling the glucose concentration and/or the sulfuric acid concentration) and/or by controlling the process conditions that exist during the process (such as use of the apparatus in which the process is performed). The glucose used here functions as an effective and yet less costly structure-directing precursor.

The silica source (TEOS) and Glucose undergo hydrolysis in presence of sulphuric acid (step 1) to produce the silica and carbon species, which is common in both thermal and hydrothermal methods (as described in example 1 and example 3). Further, sulphuric acid also acts as mediator to facilitate interaction between carbon moiety and silica moiety as the direct interaction between lypophilic carbon species and hydrophilic silica species is not possible. Here, sulphuric acid acts as sulfonation agent and the interaction of sulphuric acid with unsaturated cyclic carbon moiety creates the polarity in the molecule. Now, the sulfonyl bearing carbon moiety can easity interact with the silica specis to form carbon-silica moiety. This is called simultaneous carbonization and sulfonation.

This is not the case with two-step carbonization and sulfonation commonly described in the kwown prior art, where first the carbon moeity is thermally treated to obtain concentrated cyclic carbon bearing only limited number of —OH groups, followed by sulfonation in the second step that causes substitution of —OH groups with —SO3H. Hence the creation of sulfonyl groups is limited by the less availability of the —OH groups on the densely condensed carbon moiety caused by prior thermal treatments. So, the advantage of the present invention is to facilitate interaction between carbon moiety and sulphuric acid, right from the initial step of glucose hydrolysis, so that —SO3H groups get more —OH groups for their interaction.

In accordance with one preferred embodiment of the present invention, the process of preparing a mesoporous silica material comprising:
(a) gradually mixing a saccharide with a silica source and a sulfuric acid to form a reaction mixture, wherein a ratio between saccharide and the silica source is in the range of about 0.385 to about 4.25 and a quantity of the sulphuric acid is in the range of 0.234 to 1.020 M;
(b) allowing a hydrolyzing reaction to progress in the mixture reaction by maintaining the reaction mixture at a temperature in the range of about 298 K to 320 K for a period in the range of about 2 to about 5 hours to effect hydrolyzation thereby to obtain a gel;

(c) treating the gel thus obtained in step (b) at a temperature in the range of about 350 K to about 423 K for a period in the range of about 12 hours to about 18 hours to obtain a bulk solid mass;

(d) heating the bulk solid mass as obtained in (c) at a temperature in range of about 473 K to about 573 K for a period in the range of about 4 hours to about 8 hours under nitrogen gas to obtain the sulfonated carbon silica (SCS) composite (a) gradually mixing a saccharide with a silica source and a sulphonizing agent to form a mixture; and (e) calcining the sulfonated carbon silica composite to obtain mesoporous silica material.

In accordance with another preferred embodiment of the present invention, the process for preparing sulfonated carbon silica (SCS) composite more specifically comprises the sequential steps of:

a. drop wise addition of 20 g to 80 g glucose dissolved in 20 g to 80 g water in to the beaker containing 20 g to 80 g TEOS under stirring;

b. followed by the drop-wise addition of 20 g to 100 g concentrated sulfuric acid (98%)) under vigorous stirring to obtain the mixture containing 1 mole TEOS, 0.385 to 4.25 mole of glucose, 4.8 to 23.12 mole of water and 0.88 to 5.33 mole of $H_2SO_4$;

c. keeping the resultant mixture at 350 K to 423 K for 12 to 18 hours for its drying (described in example 1) or treatment inside Teflon-lined autoclave at 350 K to 423 K for 12 to 18 hours (described in example 4);

d. followed by heating the mixture at 473 K to 573 K for facilitating sulfonation and carbonization reaction to produce carbon-silica-meso composite (SCS) material; and e. followed by its through washings with 2 to 8 liter of water for 2 to 3 hours to remove physically adsorbed sulfate ions, followed by its drying at 293 K to 423 K temperature for 2 to 6 hours and drying at 373 to 403 K for 2 to 6 hours.

The MS material obtained in the invention exhibits high surface area ranging from 300-800 $m^2/g$ preferably 550 $m^2/g$. In still another embodiment of the present invention, the porosity of the MS material can be varied in terms of meso pore diameter and the pore volume just by varying the concentration of glucose in the initial synthetic mixture. The MS material obtained will exhibit mesopores in the diameter range from 5 to 20 nm preferably 5.6 nm.

Glucose used can act as mesopores forming agent at the reaction conditions chosen for synthesis of MS thus avoids the use of otherwise costly structure directing agents such as surfactants and block copolymers. The process developed can produce the sulfonated carbon silica composite and hierarchical mesoporous silica of desired pore diameter by varying the glucose concentration.

Further, sulfonated carbon silica composite having catalytic applications for the two industrially important reactions viz. tertiary butylation of phenol and the acetalization of glycerol for the production of solketal. In addition to this, the SCS materials synthesized in the present method are potential source for the production of high surface area hierarchical mesoporous silica (MS) materials required for immobilization of various acid and metal functionalities related to material and catalyst development applications. The facile synthesis method of the present invention produced high quality SCS and MS materials through the novel procedure of single step carbonization and sulfonation of a common chemical glucose obtained from the renewable source.

In the present intention, attention has been paid to the use of low-cost chemicals available from renewable sources viz glucose as a carbon source. Interestingly, the intermediate formed upon sulfonation of the carbon source acts as structure directing agent (template) to yield the sulfonated carbon silica composite (SCS) material which up on simple calcination produce the high surface area hierarchical mesoporous silica (MS). The method is advantageous as it does not require the use of any costly template and the monosaccharide glucose used can be from the biomass source which is renewable and helps in utilization of bio-derivative to avoid the use high cost ionic surfactant and block co-polymer.

In still another embodiment of the present invention, the SCS material used for the tertiary butylation of phenol exhibiting as high 50 mol % conversion with respect to phenol and >99 mol % conversion with respect to t-butyl alcohol. Further, the present invention the novel acid function bearing SCS composite material acts as a catalyst in a liquid-phase alkylation of phenol to obtain the tertiary-butyl phenol product with high conversions and selectivity.

The SCS material used for the acetalization of glycerol for solketal production give the conversion of glycerol up to 80 mol % with as high as 99% selectivity. The SCS material synthesized in the present invention also provides catalytic activity towards the conversion of Glycerol into solketal (ketal of glycerol). This process finds potential applications due to the huge formation of low value glycerol as bi-product in bio-diesel production on one hand and the high value and demand for the solketal on the other. The product solketal possesses excellent blending properties suitable for the formulation of gasoline, diesel and biodiesel fuels. This oxygenated compounds, when incorporated into standard diesel fuel, have led to a decrease in particles, hydrocarbons, carbon monoxide and unregulated aldehyde emissions. Likewise, these products can act as cold flow improvers for use in biodiesel, also reducing its viscosity. This issue is of significant importance due to the growing demand for new additives specifically for biodiesel that are biodegradable, non-toxic and renewable.

The present invention synthesize sulfonated carbon silica composite and hierarchical mesoporous silica without using any costly organic templates and uses simple low cost glucose as carbon source (saccharide) and as precursor for structure directing agent in formation of mesoporous silica. Further, the method involves the novel concept of the simple one step simultaneous carbonization and sulfonation of saccharide in presence of organic silica moiety to produce highly acidic mesoporous SCS intermediate capable of producing high surface area mesoporous silica upon simple calcination. The pore diameter and meso pore volume of the mesoporous silica can be controlled with wide range just by varying the saccharide concentration in the initial synthetic mixture so as to design the properties of the MS material for the targeted application. Thus the process uses widely available, cheaper compound "glucose", saccharide as carbon source as well as precursor for structure directing agent in the synthesis of MS.

Other and further features and advantages of the present invention will be apparent more fully from the following examples which are given by way of illustration therefore, should not be construed to limit the scope of the invention.

EXAMPLE 1

Figure 2:
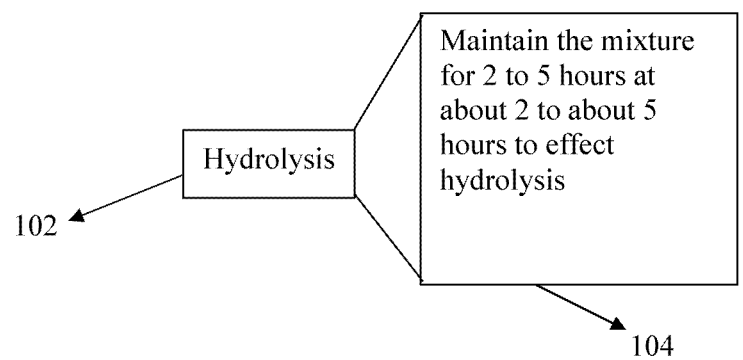
FIG. 2 illustrates details of step 102 (illustrated in FIG. 1) in accordance with the teachings of the present invention.
Figure 3:
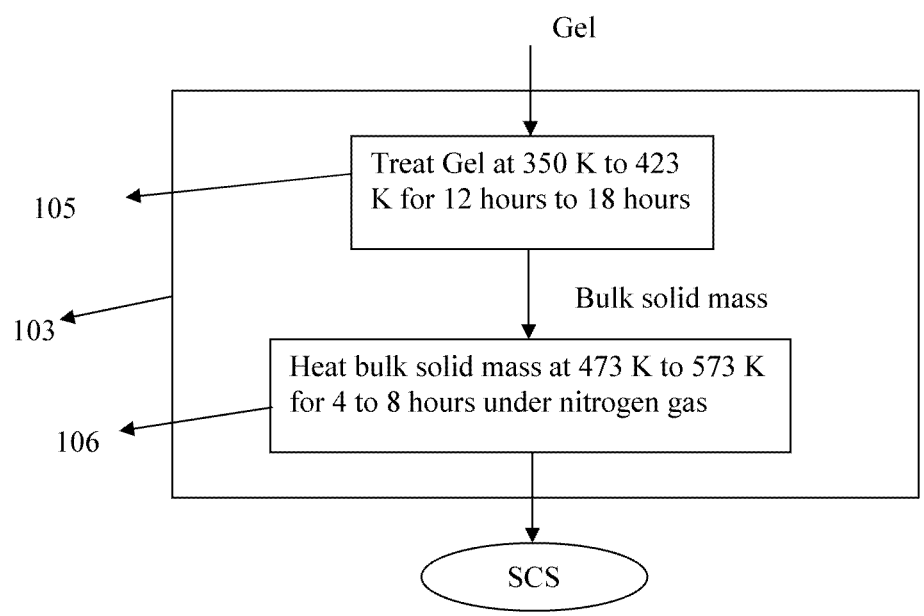
FIG. 3 illustrates details of step 103 (illustrated in FIG. 1) in accordance with a first option.

This example illustrates the synthesis of sulphonated carbon-silica composite (SCS) material through a novel and simple method following the concept of simultaneous carbonization and sulphonation, where glucose was used as carbon source for the formation of the sulphonated carbon at the optimized synthetic conditions (FIGS. 1, 2 & 3 taken together). In a typical synthesis procedure of SCS material a solution obtained by dissolving 20 g of glucose in 20 g de-ionized water was added drop-wise to the 60 g TEOS solution, followed by drop-wise addition of 23 g of concentrated sulfuric acid (98%). The solutions were continuously under vigorous stirring throughout the procedure and the resultant mixture was further allowed for mixing under stirring for 3 hours. The resultant solution was left to hydrolyze at 298 K for 2 hours and the dry gel thus obtained was heated at 393 K for 12 hours and 573 K for 4 h under nitrogen to obtain the solid form of sulfonated carbon-silica-meso composite (SCS) material, which was washed with cold followed by hot deionized water until no sulfate ions appeared in filtrate solution (by checking with barium hydroxide solution) and dried at 393 K temperature for 12 hours. The final yield of the SCS material was 15 g.

EXAMPLE 2

Figure 5:
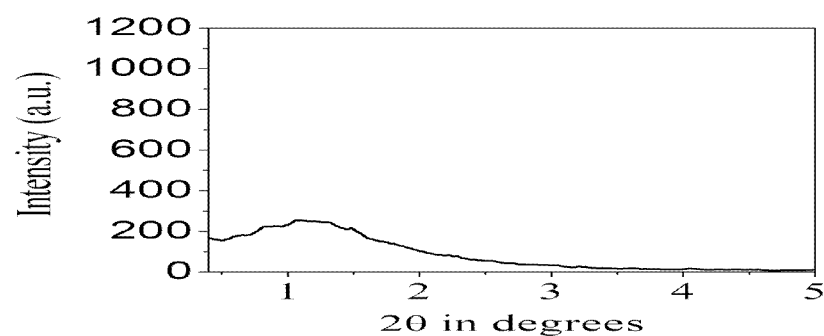
FIG. 5 is the plots of the 2 theta degree vs intensity of the low angle x-ray diffraction patterns of the SCS composite material prepared in accordance with the process described in example 1.
Figure 6:
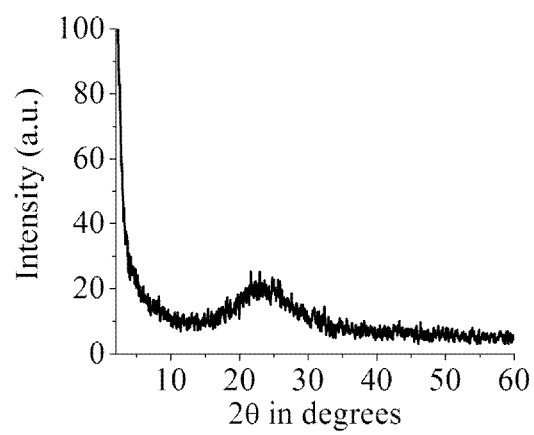
FIG. 6 is the plots of the 2 theta degree vs intensity of the wide angle x-ray diffraction patterns of the SCS composite material prepared in accordance with the process described in example 1.
Figure 7:
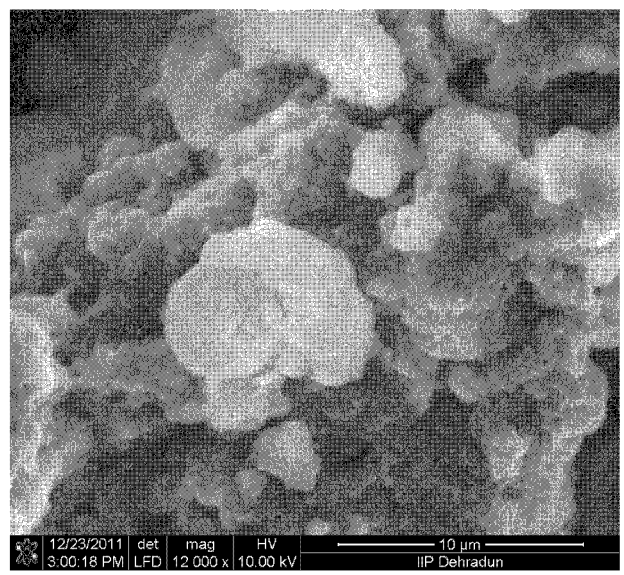
FIG. 7 is the picture of the scanning electron microgram obtained for the SCS composite material prepared in accordance with the process described in example 1.

This example illustrates the physicochemical properties and morphology of sulfonated carbon silica composite (SCS) material synthesized by the procedure described in example 1. The low angle XRD patterns given in FIG. 5 indicates the formation of mesoporous structure, while the wide angle XRD pattern of the corresponding material given in FIG. 6 indicates the formation sulfonated carbon silica composite (SCS) material. The Scanning Electron Microgram (SEM) of the resultant SCS material given in FIG. 7 shows the morphology of the SCS with porous texture.

EXAMPLE 3

This example illustrates the effect of glucose concentration on the textural properties of the sulfonated carbon-silica-mseo composite prepared by the method explained in example 1. The carbon and silica composition of the resultant SCS materials was determined by TGA analysis where the weight % of carbon in three samples having TEOS/glucose molar ratios of 1/0.385, 1/1 and 1/4 was observed to be 18 wt %, 35 wt % and 52 wt % respectively. Accordingly, the silica weight % of the corresponding samples is measured as 82 wt %, 65 wt % and 48 wt %. The same is illustrated in Table 1a.

TABLE 1a

Table shows effect of TEOS and glucose ratio on the composition of the product:

| TEOS/Glucose | Wt % of Carbon | Wt % of Silica |
|---|---|---|
| 1/0.385 | 18 | 82 |
| 1/1 | 35 | 65 |
| 1/4 | 52 | 48 |

The data given in table 1b indicates the flexibility in the properties of the synthesized material is possible to tailor the properties such as average pore diameter, mesopores volume and surface area by simple approach of varying the concentration of glucose used in the initial synthetic mixture. The data illustrates that by increasing the glucose concentration the average pore diameter first increases but, further increase in glucose concentration does not increase this value rather, the average pore diameter decreases (serial number 1 to 3), Similar trend was also observed in respect to the total pore volume. The micro pore volume is continuously increased with the glucose concentration. The data also indicates that the surface area decreases as the glucose concentration increases. Overall, this example indicates the effect of glucose concentration in the initial synthetic mixture on the formation relative contribution to the micro pores and meso pores and their collective effect on the total pore volume and surface area. The results thus provide a tool for the synthesis of SCS material with controlled pore size through changing the concentration of glucose so as to obtain the material with desired properties required for a proposed chemical reaction and has potential applications in synthesizing pore size engineered sulfonated carbon-silica-meso composite for the specific applications in catalysis and material chemistry.

TABLE 1b

Textural properties of sulfonated carbon silica composite prepared by without autoclave treatment with tunable properties:

| No | TEOS/Glucose | A | B | C | D | E | F | G | H |
|---|---|---|---|---|---|---|---|---|---|
| 1 | 1/0.385 | 779 | 220 | 539 | 0.52 | 0.10 | 0.42 | 2.6 | 0.66 |
| 2 | 1/1 | 436 | 166 | 269 | 0.61 | 0.07 | 0.54 | 5.6 | 0.96 |
| 3 | 1/4 | 425 | 274 | 151 | 0.32 | 0.11 | 0.21 | 3.0 | 0.76 |

Figure 4:
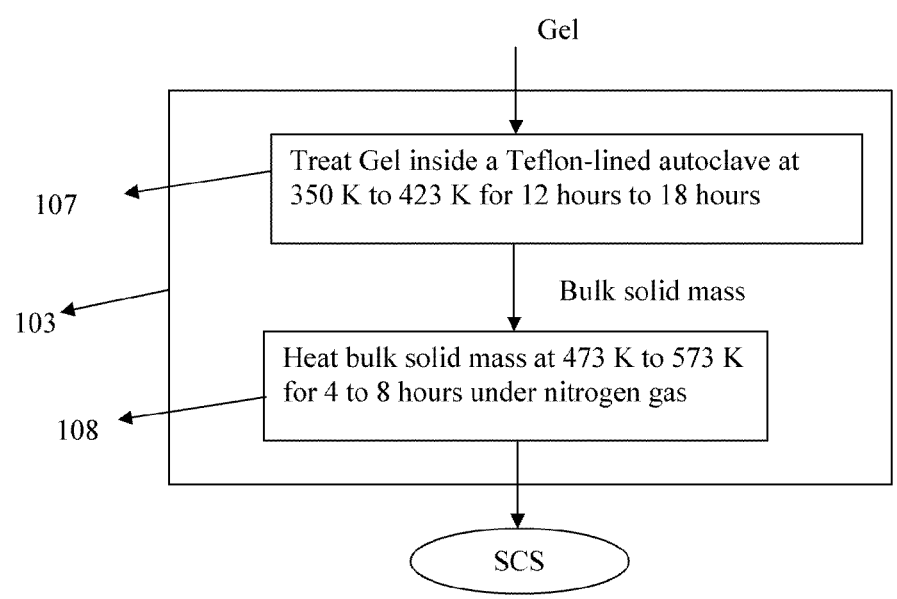
FIG. 4 illustrates details of step 103 (illustrated in FIG. 1) in accordance with a second option.
Figure 8:
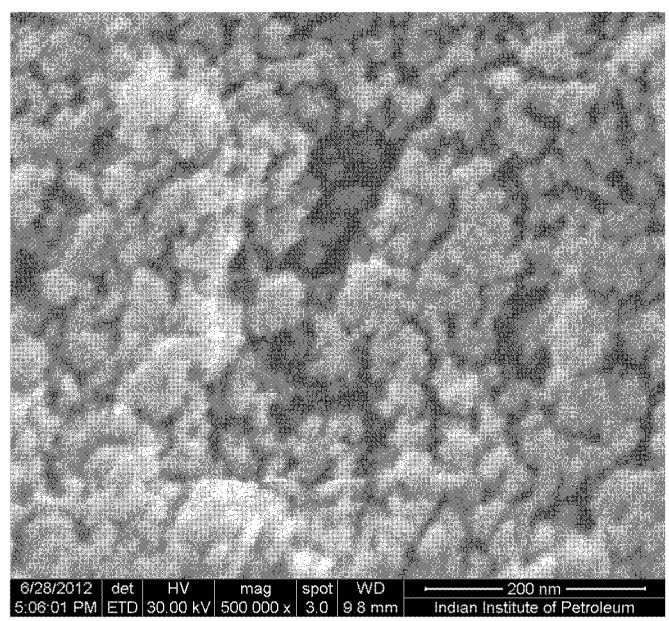
FIG. 8 is the picture of the scanning electron microgram obtained for the SCS composite material prepared in accordance with the process described in example 4.

TEOS/Glucose being in molar ratio;
A BET surface area in $m^2g^{-1}$;
B Micropore surface area calculated from t-plot in $m^2g^{-1}$;
C Mesopore surface area were calculated as A-B in $m^2g^{-1}$;
D Total pore volume taken from the volume of $N_2$ adsorbed at $P/P_0 = 0.995$ in $cm^3g^{-1}$;
E Micropore volume calculated from t-plot in $cm^3g^{-1}$;
F Mesopore volume were calculated as D-E in $cm^3g^{-1}$;
G BJH adsorption average pore diameter in nm; and
H acidity measured by temperature programmed desorption of ammonia in m.mol $NH_3$/g catalyst.

ple illustrates the synthesis of SCS material by a new method different from that described in example 1. The main difference in the two methods lies in adopting the additional step of hydrothermal treatment of the final gel in an autoclave in case of the present method (FIGS. 1, 2 & 4 taken together). In a typical synthesis of SCS material a solution obtained by dissolving 20 g of glucose in 20 g de-ionized water was added drop-wise to the 60 g TEOS solution, followed by drop-wise addition of 23 g of concentrated sulfuric acid (98%). The solutions were continuously under vigorous stirring through out the procedure and the resultant mixture was further allowed for mixing under stirring for 3 hours. The resultant solution was left to hydrolyze at 298 K for 2 hours and the gel thus obtained was treated inside the Teflon-lined autoclave at 423 K for 15 hours and the resultant black solid mass was treated at about 573 K for 4 hours under nitrogen gas to obtain the solid sulfonated carbon-silica-meso composite (SCS) material, which was washed by cold followed by hot deionized water until no sulfate ions appeared in filtrate solution (by checking with barium hydroxide solution) and dried at 393 K temperature for 12 hours. Final yield of the SCS material was 14 g. The Scanning Electron Microgram (SEM) of the resultant SCS material given in FIG. 8 shows the morphology of the SCS with porous texture.

EXAMPLE 5

The carbon and silica composition of the resultant SCS materials was determined by TGA analysis where the weight % of carbon in three samples having TEOS/glucose molar ratios of 1/0.385, 1/1 and 1/4 was observed to be 22 wt %, 36 wt % and 54 wt % respectively. Accordingly, the silica weight % of the corresponding samples is measured as 78 wt %, 64 wt % and 46 wt %. This is demonstrated in Table 2a.

TABLE 2a

Table shows effect of TEOS and glucose ratio on the composition of the product:

| TEOS/Glucose | Wt % of Carbon | Wt % of Silica |
|---|---|---|
| 1/0.385 | 22 | 78 |
| 1/1 | 36 | 64 |
| 1/4 | 54 | 46 | ple illustrates the effect of glucose concentration on the porosity and acidity of the SCS composite materials synthesized by the method described in example 4 with tunable porosity in terms of average pore diameter, mesopores volume and surface area. Wherein, by varying the glucose concentration the porosity is varied as data given in Table 2b. The data illustrates the continuous increase in micropore volume with simultaneous decrease in mesopores volume occurring by increasing the glucose concentration in the synthetic mixture. This is because of the fact that glucose is a precursor for the formation of micro porous carbon material, and the excess glucose contributes to the formation of additional micropores that are responsible for the increase of micro pore volume in the composite material. This phenomenon results in the decrease of average pore diameter of the pores in the final composite material. The data given in table 2b indeed indicates the decrease of the average pore diameter (serial number 1 to 3) by increasing the glucose concentration. The data indicates glucose-dependent properties of the SCS material and the possibility of exploring the glucose amount to design the SCS for the desired catalytic applications.

TABLE 2b

Textural properties of SCS prepared by method described in example 4:

| No | TEOS/Glucose | A | B | C | D | E | F | G | H |
|---|---|---|---|---|---|---|---|---|---|
| 1 | 1/0.385 | 238 | 21 | 217 | 0.82 | 0.0072 | 0.813 | 13.8 | 0.98 |
| 2 | 1/1 | 176 | 82 | 94 | 0.25 | 0.039 | 0.211 | 5.9 | 0.95 |
| 3 | 1/4 | 242 | 119 | 143 | 0.35 | 0.0497 | 0.30 | 5.7 | 1.29 |

TEOS/Glucose being in molar ratio;
A BET surface area in $m^2g^{-1}$;
B Micropore surface area calculated from t-plot in $m^2g^{-1}$;
C Mesopore surface area were calculated as A-B in $m^2g^{-1}$;
D Total pore volume taken from the volume of $N_2$ adsorbed at $P/P_0 = 0.995$ in $cm^3g^{-1}$;
E Micropore volume calculated from t-plot in $cm^3g^{-1}$;
F Mesopore volume were calculated as D-E in $cm^3g^{-1}$;
G BJH adsorption average pore diameter in nm; and
H acidity measured by temperature programmed desorption of ammonia in m.mol $NH_3$/g catalyst.

EXAMPLE 6

This example illustrates comparison in the properties of SCS material synthesized by two methods described in example 1 and example 4 (Table 3). It is interesting to see that the hydrothermal treatment in autoclave adopted in the latter method resulted in significant variation in the micro and meso pore volume distribution. The micro pore volume is decreased from 0.10 $cm^3 g^{-1}$ to 0.0072 $cm^3 g^{-1}$, while that of mesopores is increased significantly from 0.420 $cm^3 g^{-1}$ to 0.813 $cm^3 g^{-1}$ in the second method. This has resulted in the significant increase in average diameter of the pores from 2.6 nm to 13.8 nm. However, the surface area of the SCS was decreased in the second method due to the decrease in micro pores. The acidity of SCS measured by Temperature Programmed Desorption (TPD) indicates a marginal increase in acidity of the material synthesized in example 4. Overall this example describes hydrothermal treatment as a additional tool to design the porosity and acidity properties of the SCS material. The flow chart of the both the method is given in FIG. 5.

TABLE 3

Comparisons of the textural properties of SCS materials prepared by two different methods described in example 1 and example 4:

| No | TEOS/Glucose | A | B | C | D | E | F | G | H |
|---|---|---|---|---|---|---|---|---|---|
| M1 | 1/0.385 | 779 | 220 | 539 | 0.52 | 0.10 | 0.42 | 2.6 | 0.66 |
| M2 | 1/0.385 | 238 | 21 | 217 | 0.82 | 0.0072 | 0.813 | 13.8 | 0.98 |

TEOS/Glucose being in molar ratio;
A BET surface area in $m^2g^{-1}$;
B Micropore surface area calculated from t-plot in $m^2g^{-1}$;
C Mesopore surface area were calculated as A-B in $m^2g^{-1}$;
D Total pore volume taken from the volume of $N_2$ adsorbed at $P/P_0 = 0.995$ in $cm^3g^{-1}$;
E Micropore volume calculated from t-plot in $cm^3g^{-1}$;
F Mesopore volume were calculated as D-E in $cm^3g^{-1}$;
G BJH adsorption average pore diameter in nm; and
H acidity measured by temperature programmed desorption of ammonia in m.mol $NH_3$/g catalyst.

EXAMPLE 7

This example illustrates the effect of synthetic conditions on the morphology of the SCS material obtained. The Scanning Electron Microgram (SEM) of the SCS samples obtained by two methods is given in FIGS. 7 and 8. The SCS of the first method (followed by the procedure given described in example 1) exhibits the formation of larger size composite aggregates (FIG. 7), while that of the second method (described in example 4) exhibits nano-range composite aggregates (FIG. 8). A common phenomenon observed in SCS of the both the methods is the increase in the size of composite aggregates by increasing the concentration of glucose. Hence, the concentration of glucose can be used as a prime synthetic tool for tailoring the aggregate size of the SCS, especially to synthesize the nano composite materials useful for potential catalytic applications such as those described in examples 9 and 10.

EXAMPLE 8

Figure 9:
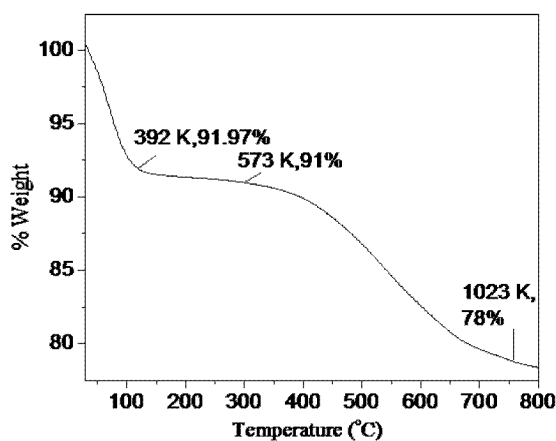
FIG. 9 is the plot of the percent weight loss vs temperature of thermo gravimetric analysis patterns of the SCS composite material as described in example 8.

This example illustrates the thermal stability of the SCS material analyzed by thermo-gravimetric analysis (TGA) method, where the weight loss of the material is measured with respect to the increase of the temperature. As shown in FIG. 9, the material gives the initial weight loss of about 8 wt % related to the removal of moisture and no weight loss between 373 K to 573 K indicates that SCS material is thermally stable up to 573 K. However, above this temperature further weight loss of 14 wt % related to the decomposition of the carbon material was occurred. Overall, the result indicates the structural stability of the SCS up to the 573 K and envisions its potential catalytic applications.

EXAMPLE 9

This example illustrates catalytic applications of the SCS material for the tertiary butylation of phenol that was carried out in round bottom flask equipped with reflux condenser joint with freezing pump for the continuous water supply. In a typical procedure, 200 mg SCS catalyst was taken in a round bottom flask to whom phenol (Merk India Ltd.) and tertiary butyl alcohol (Merk India Ltd.) were added in 1:2.5 molar ratio, followed by increasing of the reaction temperature to 393 K and the reaction was conducted at this temperature for 9 hours. The product obtained after the reaction was collected and the catalyst was separated by filtration washed with ethanol dried at 373 K and reused for three times. The reaction conditions and product yields given in table 4 clearly indicates the effectiveness of the catalyst in exhibiting as high 50 mol % conversion with respect to phenol and >99 mol % conversion with respect to t-butyl alcohol.

TABLE 4

Catalytic performance of the SCS material for the tertiary butylation of phenol:

| Reusabilty (Cycle) | Reaction time (h) | Conversion of phenol (mol %) | Selectivity of product (mol %) | | |
|---|---|---|---|---|---|
| | | | 2-TBP | 4-TBP | 2,4-DTBP |
| 1 | 9 | 50 | 52 | 30 | 18 |
| 2 | 9 | 48 | 52 | 31 | 17 |
| 3 | 9 | 49 | 53 | 29 | 18 |

EXAMPLE 10

This example illustrates catalytic applications of the SCS material for the acetalization of glycerol to solketal. In a typical experiment, 0.25 gm of catalyst (5% of glycerol weight) was taken in a round bottom flask and 18.91 g of acetone and 5 g of glycerol with glycerol to acetone molar ratio 1:6 was added to it and refluxed the reactant mixture at 70° C. for different time durations viz. from 30 min to 4 h. The product thus obtained has been analyzed by Gas chromatography. The data given in table 5 indicates as high as 80 mol % conversion of glycerol with almost complete selectivity to solketal, thus envisions the potential catalytic applications of the SCS material.

TABLE 5

Catalytic performance of SCS material for the acetalization of glycerol for solketal synthesis:

| Reusabilty (Cycle) | Reaction time (h) | Conversion of Glycerol (mol %) | Selectivity of product (mol %) | |
|---|---|---|---|---|
| | | | Solketal | Other |
| 1 | 0.5 | 80 | 98 | 2 |
| 2 | 0.5 | 79 | 99 | 1 |
| 3 | 0.5 | 78 | 99 | 1 |

EXAMPLE 11

Figure 10:
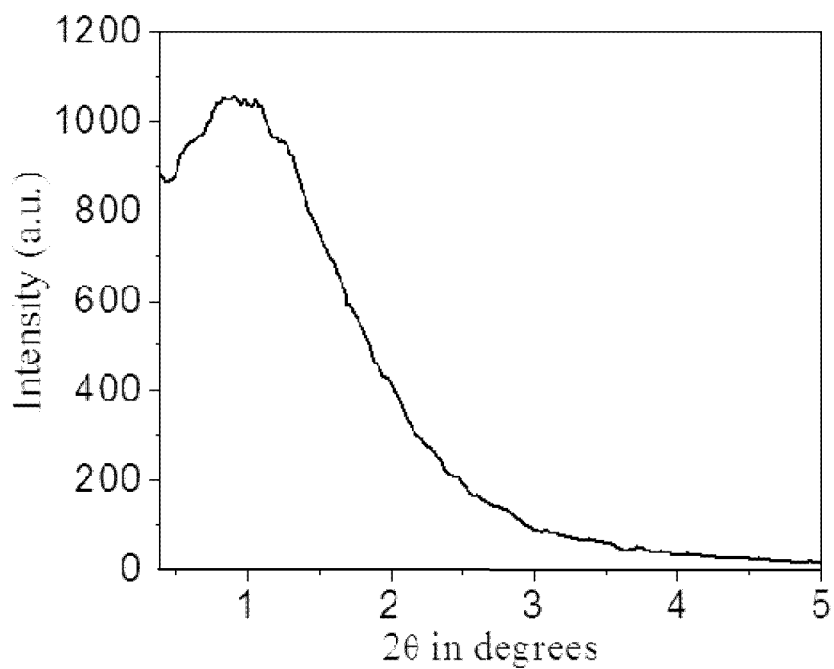
FIG. 10 is the plot of the 2 theta degree vs intensity of the low angle x-ray diffraction patterns of the hierarchical mesoporous silica (MS) prepared in accordance with the process described in example 11.
Figure 11:
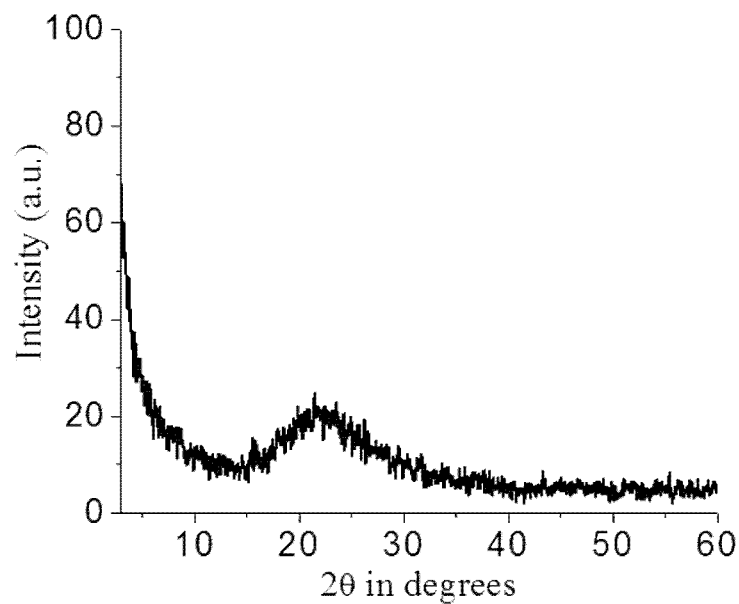
FIG. 11 is the plot of the 2 theta degree vs intensity of the wide angle x-ray diffraction patterns of the hierarchical mesoporous silica (MS) prepared in accordance with the process described in example 11.
Figure 12:
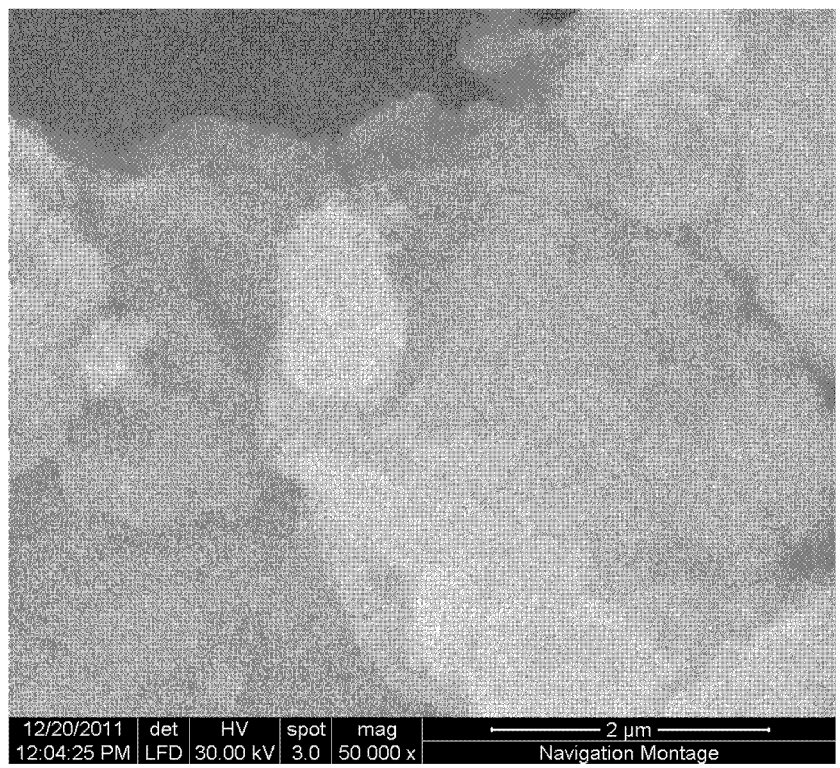
FIG. 12 is the picture of the scanning electron microgram obtained for hierarchical mesoporous silica prepared in accordance with the process described in example 11.

This example illustrates the synthesis of hierarchical mesoporous silica (MS) useful for the functionalization with various acid and metal groups for catalytic applications. In a typical procedure of MS synthesis, the SCS materials synthesized by method described in example 1 and example 4 are calcined at 873 K for 6 h to remove the carbon moiety of the SCS. The formation of MS from SCS is confirmed from the XRD patterns. The low angle XRD patterns given in FIG. 10 indicates the formation of mesoporous structure, while the wide angle XRD pattern of the corresponding material given in FIG. 11 indicates the formation amorphous hierarchical mesoporous silica. The Scanning Electron Microgram (SEM) of the resultant MS material given in FIG. 12 shows the morphology of the MS with porous texture. The composition MS obtained after the complete removal of carbon content of the SCS composite by calcination consists of 100% silica (no other compound other than $SiO_2$).

EXAMPLE 12

This example illustrates the textural properties of the mesoporous silica developed from the SCS material with tunable porosity in terms of average pore diameter, mesopores volume and surface area by simple approach of varying the concentration of glucose used in the initial synthetic mixture, where, by varying the glucose concentration the porosity is varied as illustrated by the data given in table 6. The data illustrates that the average pore diameter increases by increasing the glucose concentration but the micro porous surface area is first increases then decreases. The data indicates the occurrence of pore size control, through changing the concentration glucose so as to obtain the material with tunable properties and has potential applications in synthesizing pore size engineered mesoporous silica for the specific applications in catalysis and material chemistry.

TABLE 6

Textural properties of mesoporous silica with tunable properties:

| No | TEOS/ Glucose | A | B | C | D | E | F | G |
|---|---|---|---|---|---|---|---|---|
| 1 | 1/0.385 | 656.47 | 0 | 656.47 | 0.87 | 0.0 | 0.87 | 5.3 |
| 2 | 1/1 | 419 | 41 | 378 | 0.66 | 0.01 | 0.65 | 6.6 |
| 3 | 1/4 | 345 | 11 | 334 | 0.67 | .001 | 0.669 | 7.7 |

TEOS/Glucose being in molar ratio;
A BET surface area in $m^2g^{-1}$;
B Micropore surface area calculated from t-plot in $m^2g^{-1}$;
C Mesopore surface area were calculated as A - B in $m^2g^{-1}$;
D Total pore volume taken from the volume of $N_2$ adsorbed at $P/P_0 = 0.995$ in $cm^3g^{-1}$;
E Micropore volume calculated from t-plot in $cm^3g$-1;
F Mesopore volume were calculated as D-E in $cm^3g^{-1}$; and
G BJH adsorption average pore diameter in nm.

It may be noted that the embodiments illustrated and discussed in this specification are intended only to teach to those skilled in the art the best way known to the Inventors to make and use the invention. Figures may not have been drawn to scale. In describing embodiments of the Invention, specific terminology is employed merely for the sake of clarity. However, the invention is not intended to be restricted to specific terminology so-used. The above-described embodiments of the invention may be modified or varied, without departing from the invention, as appreciated by those skilled in the art in light of the above teachings. It is therefore understood that, within the scope of the claims and their equivalents, the invention may be practiced otherwise than as specifically described.

The invention claimed is:

1. A process of preparing a sulfonated carbon silica (SCS) composite comprising:
    (a) gradually mixing a saccharide with a silica source and a sulfuric acid to form a reaction mixture, wherein a ratio between saccharide and the silica source is in the range of about 0.385 to about 4.25 on a molar basis and sulphuric acid in the range of 0.234 to 1.020M;
    (b) allowing a hydrolyzing reaction to progress in the reaction mixture by maintaining the reaction mixture at a temperature in the range of about 298 K to 320 K for a period in the range of about 2 to about 5 hours to effect hydrolyzation thereby to obtain a gel;

(c) treating the gel thus obtained in step (b) at a temperature in the range of about 350 K to about 423 K for a period in the range of about 12 hours to about 18 hours to obtain a bulk solid mass; and (d) heating the bulk solid mass as obtained in (c) at a temperature in range of about 473 K to about 573 K for a period in the range of about 4 hours to about 8 hours under nitrogen gas to obtain the sulfonated carbon silica (SCS) composite.

2. The process according to claim 1, wherein step (c) comprises treating the gel as obtained in step (b) inside a Teflon-lined autoclave at a temperature in the range of about 350 K to about 423 K for a period in the range of about 12 hours to about 18 hours to obtain bulk solid mass.

3. The process according to claim 1, further comprising washing the sulfonated carbon silica composite at least once.

4. The process according to claim 3, further comprising drying the sulfonated carbon silica composite.

5. The process according to claim 3, wherein the washing is carried out for a period in the range of about 2 hours to about 3 hours.

6. The process according to claim 4, comprising drying at a temperature in the range of about 293 K to about 423 K for a period in the range of about 2 hours to about 6 hours and further drying at a temperature in the range of about 373 K to 403 about K for a period in the range of about 2 hours to about 6 hours.

7. The process according to claim 1, wherein said saccharide is selected from the group consisting of glucose, fructose and maltose.

8. The process according to claim 1, wherein said saccharide is glucose.

9. The process according to claim 1, wherein the silica source is selected from the group consisting of fumed silica, tetra-methyl ortho-silicate and tetra-propyl ortho silicate.

10. The process according to claim 1, wherein the silica source is tetra-ethyl ortho-silicate.

11. The process as claimed in claim 1, wherein the sulfonated carbon silica (SCS) composite thus produced comprises a hydrophobic inner core formed of carbons and a hydrophilic shell formed of silica matrix, said carbon being present in the range of 18% to 54% and silica in the range of 46 to 82%; said hydrophobic inner core formed of carbon atoms bearing thereupon hydrophilic sulfonyl groups, wherein amount of sulfonyl groups present is such that it imparts an overall acidity at least about 1.29 mmol $NH_3$/g catal to the sulfonated carbon silica (SCS) composite, and wherein the ratio between the total BET surface area to the mesopore surface area is in the range of 1.09 to 2.8; and the micropore surface area to the mesopore surface area is in the range of 0.09 to 1.82.

12. The process as claimed in claim 1, wherein said SCS composite exhibits surface area in the range of 150-800 m2/g.

13. The process as claimed in claim 1, wherein SCS composite exhibits mesopore diameter in the range of 2.6 to 15 nm.

14. The process as claimed in claim 1, wherein SCS composite exhibits surface area of about 650 m2/g.

15. The process as claimed in claim 1, wherein SCS composite exhibits mesopore diameter of about 5.6 nm.

16. The process as claimed in claim 1, wherein SCS composite exhibits structural stability up to about 573 K as determined by thermo gravimetric analysis.

17. A process of preparing a mesoporous silica material comprising:

(a) gradually mixing a saccharide with a silica source and a sulfuric acid to form a reaction mixture, wherein a ratio between saccharide and the silica source is in the range of about 0.385 to about 4.25 on a molar basis and sulphuric acid in the range of 0.234 to 1.020M;

(b) allowing a hydrolyzing reaction to progress in the reaction mixture by maintaining the reaction mixture at a temperature in the range of about 298 K to 320 K for a period in the range of about 2 to about 5 hours to effect hydrolyzation thereby to obtain a gel;

(c) treating the gel thus obtained in step (b) at a temperature in the range of about 350 K to about 423 K for a period in the range of about 12 hours to about 18 hours to obtain a bulk solid mass;

(d) heating the bulk solid mass as obtained in (c) at a temperature in range of about 473 K to about 573 K for a period in the range of about 4 hours to about 8 hours under nitrogen gas to obtain a sulfonated carbon silica (SCS) composite; and (e) calcining the sulfonated carbon silica composite to obtain mesoporous silica material.

* * * * *

UNITED STATES PATENT AND TRADEMARK OFFICE
CERTIFICATE OF CORRECTION

| | | |
|---|---|---|
| PATENT NO. | : 8,722,573 B2 | Page 1 of 1 |
| APPLICATION NO. | : 13/623775 | |
| DATED | : May 13, 2014 | |
| INVENTOR(S) | : Nagabhatla Viswanadham | |

It is certified that error appears in the above-identified patent and that said Letters Patent is hereby corrected as shown below:

IN THE SPECIFICATION:

In column 1 at line 4, Below title insert --RELATED APPLICATIONS    This application claims the benefit of Indian Application No.: 2597/DEL/2012, filed August 22, 2012.--.

In column 4 at line 19, Change "403 about K" to --about 403 K--.

In column 7 at line 44, Change "liter" to --liters--.

In column 8 at line 20, Change "CSC" to --SCS--.

In column 8 at line 37, Change "lypophilic" to --lipophilic--.

In column 8 at line 41, Change "easity" to --easily--.

In column 8 at line 42, Change "specis" to --species--.

In column 8 at line 45, Change "kwown" to --known--.

In column 8 at line 46, Change "moeity" to --moiety--.

In column 9 at line 37, Change "liter" to --liters--.

In column 12 at line 17 (approx.), Above "TABLE 1b" insert --EXAMPLE 4--.

In column 12 at line 35, Change "ple" to --This example--.

In column 12 at lines 44-45 (approx.), Change "through out" to --throughout--.

In column 13 at line 15 (approx.), Change "ple" to --This example--.

In column 15 at line 3, Change "Merk" to --Merck--.

In column 15 at line 4, Change "Merk" to --Merck--.

IN THE CLAIMS:

In column 17 at line 28, In Claim 6, change "403 about K" to --about 403 K--.

Signed and Sealed this
Twenty-third Day of December, 2014

Michelle K. Lee
*Deputy Director of the United States Patent and Trademark Office*